United States Patent [19]

Harrison

[11] 4,445,089

[45] Apr. 24, 1984

[54] DETECTION OF SURFACE CRACKS NEAR A WORKPIECE FASTENER HOLE BY MEANS OF A ROTATABLE PROBE

[75] Inventor: David J. Harrison, Farnham, England

[73] Assignee: The Secretary of State for Defence in Her Britannic Majesty's Government of the United Kingdom of Great Britain and Northern Ireland, London, England

[21] Appl. No.: 354,041

[22] Filed: Mar. 2, 1982

Related U.S. Application Data

[63] Continuation of Ser. No. 68,392, Aug. 21, 1979, abandoned.

[30] Foreign Application Priority Data

Aug. 21, 1978 [GB] United Kingdom ............... 33980/78

[51] Int. Cl.³ ...................... G01R 33/12; G01N 27/82
[52] U.S. Cl. .................................... 324/238; 324/232; 324/262
[58] Field of Search ................ 324/202, 207, 219–221, 324/228–240, 242, 243, 260–262, 200

[56] References Cited

U.S. PATENT DOCUMENTS

| | | | |
|---|---|---|---|
| 1,459,970 | 6/1923 | Burrows | 324/228 |
| 2,266,620 | 12/1941 | Coffman | 324/230 X |
| 3,109,139 | 10/1963 | Branker | 324/240 |
| 3,165,726 | 1/1965 | Riley et al. | 324/229 X |
| 3,302,105 | 1/1967 | Libby et al. | 324/233 |
| 3,449,664 | 6/1969 | Smith | 324/235 |
| 3,492,670 | 1/1970 | Ault et al. | 324/260 |
| 3,497,799 | 2/1970 | Harmon | 324/237 |
| 3,535,625 | 10/1970 | Pratt | 324/233 |
| 3,718,855 | 2/1973 | Rogel et al. | 324/202 |
| 3,831,084 | 8/1974 | Scalese et al. | 324/260 |
| 4,084,136 | 4/1978 | Libby et al. | 324/238 |
| 4,095,181 | 6/1978 | Harris et al. | 324/238 |
| 4,204,159 | 5/1980 | Sarian et al. | 324/232 |

FOREIGN PATENT DOCUMENTS 573182 11/1945 United Kingdom ............... 324/228

Primary Examiner—Gerard R. Strecker
Attorney, Agent, or Firm—Cushman, Darby & Cushman

[57] ABSTRACT

Apparatus for the detection of cracks or other defects near the surface of a conducting engineering material of interest includes a magnetic probe having two sites which in operation act as magnetic poles on the same side of the probe such that an external magnetic field extends between them principally in a region adjacent to that one side of the probe, means for rotating the probe about an axis spaced from the mid-point between the two sites, whereby when the probe is adjacent to the surface of an engineering material of interest occupying the region with the axis substantially perpendicular to the surface the magnetic field is able to penetrate the surface and rotate beneath it about the axis causing energy associated with the magnetic field to be dissipated in the material, and means for detecting a change caused by a defect in the material, to the dissipated energy.

7 Claims, 4 Drawing Figures

DETECTION OF SURFACE CRACKS NEAR A WORKPIECE FASTENER HOLE BY MEANS OF A ROTATABLE PROBE

This is a continuation of application Ser. No. 68,392 filed Aug. 21, 1979, now abandoned.

The present invention relates to apparatus for the detection of defects in engineering materials.

In certain environments cracks and other defects which can form in engineering materials structures can present serious problems and their early detection is desirable. For example, the frame of an aircraft usually comprises a metallic layer known as the outer skin to which is fastened an inner structure comprising a series of metallic strengthening members. Cracks occasionally form in the outer skin or in the inner structure in the vicinity of the fastener holes. Such cracks can grow rapidly leading ultimately to major structural faults, so if they are not detected soon enough disastrous consequences, such as loss of equipment and life, may result.

Inspection of an airframe for cracks near the outer surface is carried out during routine aircraft servicing. One widely used technique involves detecting the cracks ultrasonically. However this technique has the disadvantage that the layer of paint which coats the outer skin for protective purposes has to be stripped off to permit inspection and then has to be re-applied after inspection. This technique is consequently very time consuming.

Another known inspection technique involves placing an electromagnetic probe known as a ring probe in a fixed position on the outer surface of the structure at each fastener. The ring probe has a current carrying coil which sets up electromagnetically induced eddy currents near the surface of the structure in a region of similar shape to the probe. Cracks near the fastener holes increase the impedance to the eddy currents and this increase is detected, eg as a reflected impedance by measuring the voltage between the ends of the probe coil or of a separate pick up coil. The disadvantages of this technique are that the output signal obtained for a defect-free surface has first to be obtained as a reference, ie as a separate calibration measurement, so that increases in signal may be detected and also that it is difficult or impossible to distinguish between the increases due to different kinds of defect, eg cracks, burrs, rust and corrosion.

A further known inspection technique involves placing an elongate electromagnetic probe known as a 'bolt-hole probe' inside each fastener hole and spinning the probe about its axis of symmetry. The bolt-hole probe has a current carrying coil on its tip which induces eddy currents within the structure surface lateral of the hole allowing defects to be detected by changes of impedance presented to the eddy currents (similar to detection using the ring probes.) The spinning of the bolt-hole probe allows the output signal to be self-referencing. In other words the output signal for a defect-free region near the outer surface is obtained during part of the spin, so if a defect is present during another part of the same spin the output signal will change. However, as with the ultrasonic technique described above this technique has the disadvantage that the outer layer of protective paint has to be removed before and re-applied after the inspection of an airframe outer surface. In this case each fastener also has to be removed.

According to the present invention apparatus for the detection of cracks or other defects near the surface of a conducting engineering material of interest includes a magnetic probe having two sites which in operation act as magnetic poles on the same side of the probe such that an external magnetic field extends between them principally in a region adjacent to that one side of the probe, means for rotating the probe about an axis spaced from the mid-point between the two sites, whereby when the probe is adjacent to the surface of an engineering material of interest occupying the said region with the said axis substantially perpendicular to the surface the said magnetic field is able to penetrate the surface and rotate beneath it about the said axis causing energy associated with the said magnetic field to be dissipated in the material, and means for detecting a change, caused by a defect in the material, to the dissipated energy.

Preferably, the axis of rotation of the probe is substantially perpendicular to the axis joining the two sites and passes through or close to one of the two sites.

Preferably, the probe comprises a magnetic arm, eg of low loss ferrite, substantially perpendicular to the axis of rotation, having two projections, both substantially parallel to the axis of rotation, providing the two sites. In this form the projection furthest from the axis of rotation preferably carries an electrical coil to the probe constituted by the arm, its projections and the coil thus being an electromagnet.

In the last mentioned form of the invention the electromagnet may comprise a magnetic core of E-shaped cross-section the axis of rotation being along the central limb of the E, the coil being mounted on one of the outer limbs of the E and a further coil being mounted on the other outer limb of the E whereby a first external magnetic field may be provided between one outer limb and the central limb of the E and a second external magnetic field may be provided between the central limb and the other outer limb of the E.

If the probe is an electromagnet a change in the dissipated energy (associated with the rotating magnetic field) which is caused by a defect in the material of interest may be detected as a change in reflected impedance by measuring the voltage across the coil or coils. In the two coil form mentioned above the reflected impedance may conveniently be separated from other impedance by measuring the difference in voltage across the two coils. As a modification of the two coil form the probe may be multi-armed having a plurality of pairs of opposite coils, the voltages across the coils in each opposite pair being subtracted as in the two-coil form.

Alternatively a change in the dissipated energy may be detected by one or more known devices capable of externally detecting localised magnetic field perturbations beneath the surface of interest, eg magneto-resistive diodes. Two such devices may be positioned at opposite ends of the probe.

In operation of the invention in the form of the electromagnet probe as described above the probe is preferably rotated in a step-wise manner, the voltage across the coil being measured after each individual step. The probe need not carry on rotating at the end of each revolution nor even make full revolutions, eg 90° rotations may suffice. It may be rotated in a reverse sense back to a fixed starting position. Voltage measurements may or may not be made during such reversal.

Preferably the time taken for each rotation in a particular sense is at least 1 second typically 5-10 seconds. This overall figure includes an element for the rotatory movement during each step and an element for the stationary periods at the end of each step required to allow the detected signal to settle and be processed (eg as described below).

The output signals from the means for detecting a change in the voltages across the coils may be fed into a computer or microprocessor in which the profile of the set of detected signals may be characterised as belonging to a particular kind of defect. The computer or microprocessor may also be used to control the positioning of the probe adjacent to the surface and also the rotation of the probe.

Like the spinning bolt-hole probe but unlike the ring probe described above the invention has the benefit that it provides a self-referencing output signal. Further, like the ring probe but unlike the spinning bolt-hole probe the invention has the benefit that it allows inspection of a surface without prior treatment, eg removal of paint. Thus, the invention provides a previously unobtained combination of benefits.

An embodiment of the invention will now be described by way of example with reference to the accompanying drawings, in which.

Figure 1:
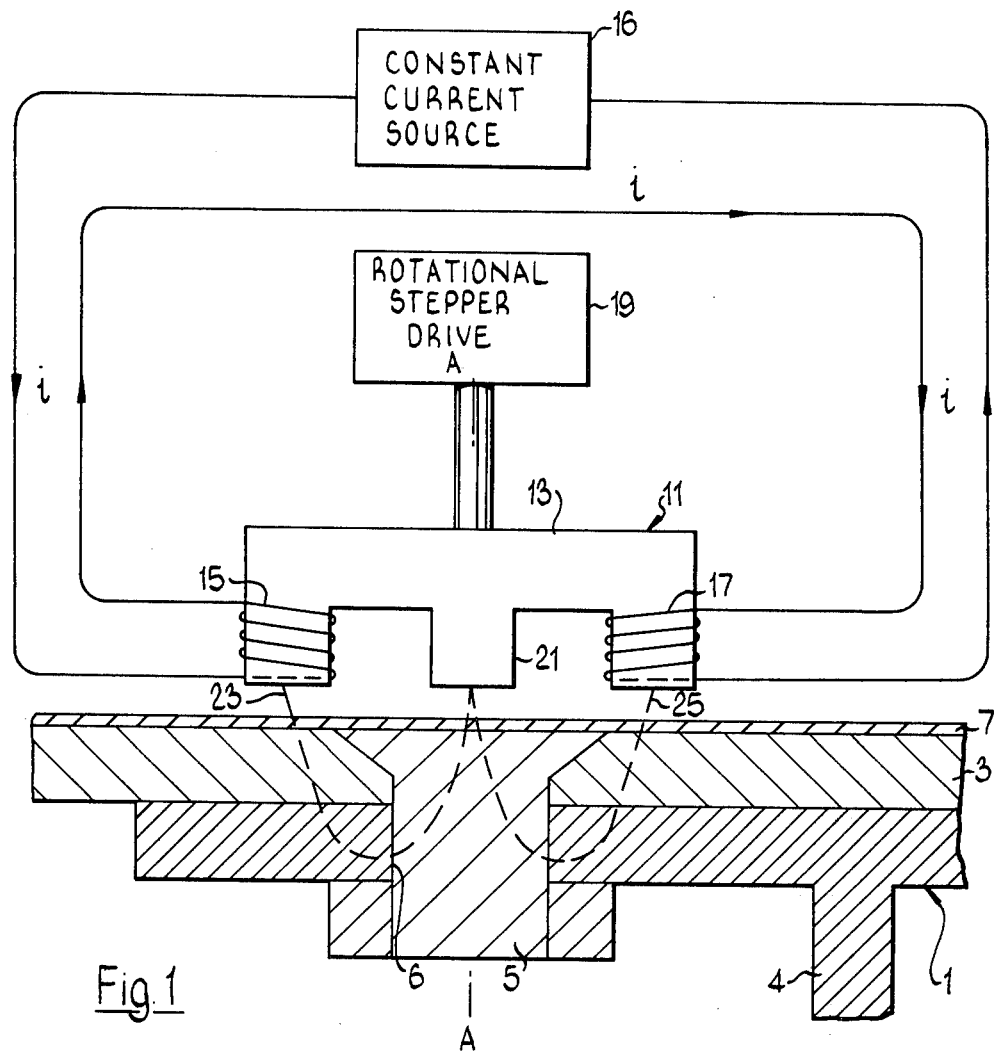
FIG. 1 is a diagram, partly in cross-sectional form and partly in schematic circuit form, of eddy current inspection apparatus.

In FIG. 1 an airframe 1 is under inspection by a probe 11. The airframe 1 comprises an inner structure 4 fastened to an outer skin 3 by a series of rivets 5 in holes 6 (one selected rivet 5 and hole 6 being shown). The inner structure 4 consists typically of a series of flanged T shaped members (one only shown) which are used to give strength to the outer skin 3. The flanged portions are known as the 'second layer'. The outer surface of the skin 3 is coated with paint 7.

The probe 11 includes an E-shaped magnetic core 13 positioned close above the airframe with its axis of symmetry denoted by the broken line A—A in FIG. 1, coinciding with the axis of the rivet 5. An electrical coil 15 is mounted on one outer limb of the core 13 whilst another electrical coil 17 of similar dimensions is mounted on the other outer limb of the core 13. The coils 15, 17 are supplied with current from a constant current source 16.

The probe 11 produces magnetic fields between the coil 15 and the central limb of the E-shaped core, denoted by the reference numeral 21 in FIG. 1, and between the coil 17 and the central limb 21. These fields are indicated for the purposes of illustration by dashed lines 23, 25 (although they are strictly three-dimensional lobes). These fields 23, 25 penetrate deepest into the airframe mid-way between limb 21 and the coils 15, 17 respectively. The size of the core 13 is chosen so that maximum penetration of the fields 23, 25 occurs close to the side wall of the holes 6 (ie the spacing between the limb 21 and the coils 15, 17 is roughly equal to the diameter of the hole 6 in the skin 3).

The probe 11 is rotated in a step-wise manner about its axis of symmetry ie the line A—A, by a conventional rotational stepper drive 19 via a shaft 21 fixed to the core 13. The probe 11 may take about 200 steps to make one overall forward rotation. After each overall forward rotation it is rotated in a reverse direction to a fixed starting position to begin the next forward rotation.

Figure 2:
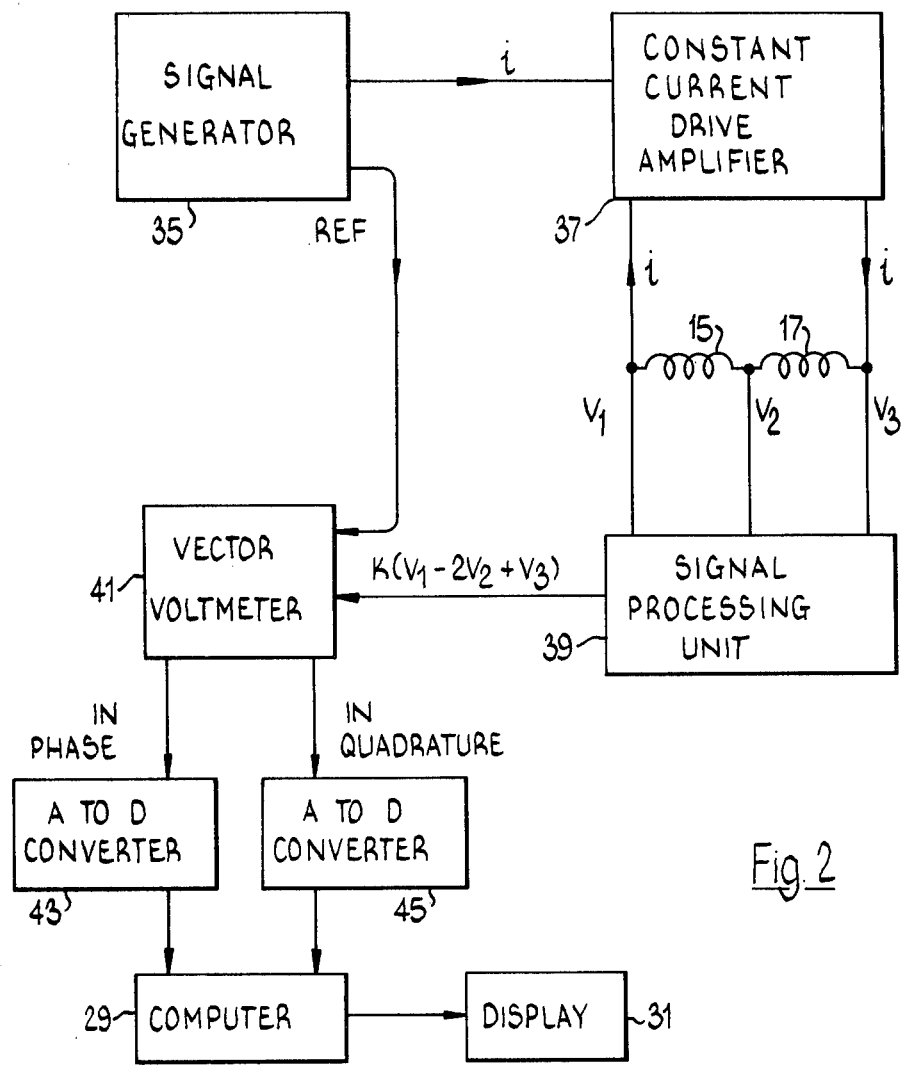
FIG. 2 is a circuit diagram of impedance measurement equipment for use with the apparatus shown in FIG. 1.

The magnetic fields 23, 25 undergo a step-wise rotational scan about the line A—A corresponding to the rotation of the probe 11. Energy is dissipated (in the form of eddy currents) in each region of the airframe through which the fields 23, 25 pass. If a crack or other defect is present in a region through which the fields 23, 25 pass it produces a change in the dissipated energy, ie a change in the impedance to the induced eddy currents (as compared with that in defect-free regions). Changes in dissipated energy are detected as follows:

The constant current source 16 (FIG. 1) consists of a signal generator 35 feeding a constant current drive amplifier 37 (FIG. 2) which drives a constant current through the coils 15 and 17 in series. The potential $V_2$ at the junction between the coils 15, 17 and the two outer potential $V_1$ and $V_3$ of the coils 15, 17 respectively are fed into a signal processing unit 39 which provides a single output equal to $k \times (V_1 - 2V_2 + V_3)$ where k is a constant, which is effectively a measure of the difference between the voltages across the two coils 15, 17. The output of the unit 39 is fed, together with a reference signal from the generator 35, into a vector voltmeter 41. This is basically a phase sensitive detector which separates its input signal into components which are in phase and in quadrature with the reference. The in phase component is supplied to an analogue to digital converter 43 and the in-quadrature component is supplied to an analogue to digital converter 45.

The complex impedance of each coil 15, 17 can be thought of as $Z = Z_1 + Z_2$ where $Z_1$ is a large, essentially constant, term due to the inherent properties of the coil, eg inductance and resistance, and also includes the reflected impedance for a defect-free surface, whilst $Z_2$ is the reflected impedance due to a crack or other defect. As each magnetic field 23, 25 is rotated changes in Z will be mainly due to changes in $Z_2$, although these changes in $Z_2$ will in general occur at different times for the two coils 15, 17. Thus the difference between the impedances of, ie the voltages across, the coils 15, 17 is measured by the signal processing unit 39 to eliminate the large $Z_1$ terms and provide a measurement of $Z_2$. In practice, the coils 15, 17 will not be identical so the unit 39 is also used to eliminate an impedance term due to the offsets.

The analogue-to-digital converters 43, 45 convert the analogue signals fed into them into a series of digits which represent respectively the real and imaginary components of the measured reflected impedances for each step of the rotation of the probe 11. These series will have overall profiles which are similar in shape but which are displaced in relative phase.

Figure 3:
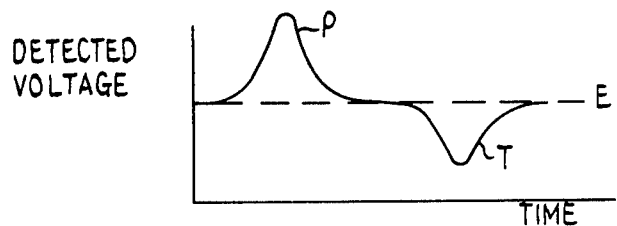
FIG. 3 is a graph of a typical output signal obtained from the apparatus of FIGS. 1 and 2.

A typical voltage waveform representing the output of one of the converters 43, 45 when a crack is present is shown in FIG. 3. For defect-free regions of the material under inspection the voltage is essentially close to a base reference level E. Where a crack is present the detected voltage rises first to a peak P and later falls to a trough T which is an inverted form of the peak P. The peak P effectively represents detection of the crack by the magnetic field 23 whilst the trough T effectively represents detection of the same crack by the magnetic field 25.

The output digits from the converters 43, 45 are fed into a digital computer 29 which stores them whilst rotation of the probe 11 is still in progress and later processes them as required.

For example the computer 29 may be used to estimate the size and position of a detected crack. The computer 29 may also take the ratio of corresponding digits in the two series to distinguish signals due to cracks from those due to other kinds of defect by comparing the result with pre-programmed sets of pattern recognition data characteristic of different defects.

The output data from the computer 29 is fed into a conventional display 31, eg a cathode ray tube or electronic or digital display.

The apparatus described with reference to FIG. 1 is sufficiently sensitive to detect cracks of 0.25 mm in length at a depth of 1.0 mm beneath the surface. However for such small cracks the signal-to-noise ratio is likely to be poor. For larger cracks, eg 0.5 mm or more in length, at this depth the signal-to-noise ratio is at an acceptable level. Detection of cracks at depths greater than 2.0 mm requires lower frequencies (for a given probe size) which result in lower sensitivity. Thus the limiting length of crack is longer at such greater depths. Nevertheless some cracks in the airframe 1 down to a depth of 5 mm or more (including cracks in the 'second layer') may be detected by the apparatus.

If the probe 11 is rotated when the axis of the probe 11 does not coincide with that of the rivet 5 a sinusoidal signal profile results in the output from the converters 43, 45, the magnitude of the sinusoidal signal depending on the amount of offset between the two axes. This signal is due to the impedance changed by the interface between the rivet 5 and skin 3. Effectively, the complex impedance component Z referred to above is not constant in this case but includes the sinusoidal components.

The computer 29 may be used to control centring of the probe 11 over the rivet 5 by calculating the direction which the probe must be moved, and the size of step required, to remove the sinusoidal component. The display 31 may be used to display the changing waveform whilst the probe 11 is being centred in this way.

In practice it is not necessary for the probe 11 to undergo a full rotational scan to centre the probe 11. It is sufficient for measurements to be taken in two positions 90° apart. The taking of the measurements may be controlled by the computer 29.

Figure 4:
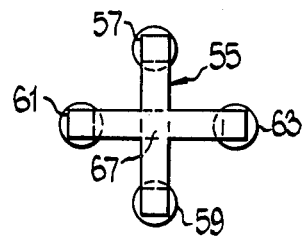
FIG. 4 is a schematic plan view of an electromagnet probe alternative to that in the FIG. 1 apparatus.

In another embodiment of the invention the probe may consist of a cross 55 as shown in plan in FIG. 4 the arms of the cross each having projections (similar to the limbs shown in FIG. 1) perpendicular to the plane of the drawing each carrying separate coils 57, 59, 61, 63. The probe also has a central projection, 67, also perpendicular to the plane of the drawing, similar to the limb 21 in FIG. 1. Thus the probe can be thought of as two E-shaped probes as shown in FIG. 1 at right angles to one another. In this case the coils on opposite arms of the cross, ie the coils 57 and 59 and the coils 61 and 63, are connected in series as a pair like the coils 15, 17 in FIG. 2 and each pair is used in the same way as the coils 15, 17, ie by feeding into similar circuitry to that shown in FIG. 2. The advantage of taking impedance measurements using more than one pair of coils in this way is that the output waveforms are obtained using a smaller number of steps (for rotation of the probe) and that computer-controlled centring of the probe is simpler because it is not necessary to make successive measurements 90° apart.

I claim:

1. Apparatus for the detection of cracks near the surface of a workpiece and adjacent to a fastener hole therein comprising:

a magnetic probe including a magnetic core having a coil mounted thereon, the core having two arms forming magnetic poles and a link portion between them, said coil being mounted on a first one of said arms, said arms and said link portion having a cross-sectional thickness perpendicular to its axis which is small compared to the spacing between said arms, whereby in operation with the surface of the workpiece adjacent to said poles a magnetic field extends between said poles and penetrates said workpiece, said magnetic field being concentrated in the region of both of said poles, the lateral spread of said magnetic field being restricted by the cross-sectional thickness of said arms and said line portion to a width which is small compared to the spacing between said poles;

a rotational stepping drive arrangement for rotating said probe in a stepwise manner about an axis of rotation substantially parallel to said arms and displaced from said first arm which axis may in use be made coincident with the axis of said fastener hole, whereby said first arm and said coil are rotationally stepped about said axis of rotation;

means for energizing said coil;

detection circuit means for generating at the end of each step of said stepped rotation a first signal representative of the energy of said magnetic field dissipated in said workpiece by detecting the energy supplied to said coil;

reference signal generator means for generating a second signal representative of the energy dissipated in the defect free regions of said workpiece;

comparator means for comparing said first and second signals and for providing a third signal representing any difference between said first and second signals;

an analog-to-digital converter for digitizing said third signal, a digital store for storing said third signal in digital form while said probe is rotating; and a display, having an input from said store, for displaying a graphical plot of the variation of said third signal with the rotational position of said probe.

2. Apparatus as claimed in claim 1 wherein said stepping drive arrangement comprises means for stepping the position of said first arm around an arcuate path and returning said first arm to a starting position by rotating said arm in the reverse direction of said stepped rotation.

3. Apparatus as claimed in claim 2 wherein the time taken for a forward rotation of said first arm is greater than 1 second.

4. Apparatus as claimed in claim 1 wherein said core is substantially E-shaped, one of the outer arms of said core being said first arm carrying said coil, the axis of rotation of said probe passing through the middle arm of said core, the other outer arm of said core carrying a second coil acting as a reference signal coil, said reference signal generator being a circuit for detecting the voltage across said second coil.

5. Apparatus as claimed in claim 1 wherein said core comprises two mutually orthogonal E-shaped members having a common central arm, each of the outer arms of said core carrying a coil, the energizing means being connected to each of the coils and the comparator means being arranged to compare the voltages across opposite pairs of said coils.

6. Apparatus as claimed in claim 1 wherein the apparatus comprises a computer device incorporating said store which computer device also includes a pattern recognition processor for comparing said third signal with a pre-programmed set of data characteristic of a signal due to a crack in said workpiece.

7. A method for detecting cracks near a fastener hole provided in the surface of a conducting workpiece including the steps of:

(a) locating a rotatable probe above said hole with the axis of rotation of said probe substantially coincident with the axis of said hole, said probe including a magnetic probe including a coil mounted on a magnetic core, the core being shaped so as to provide two arms forming separated magnetic poles, said arms having at said poles a cross-sectional area which is small compared with the distance between said poles to form a field concentrated in the region of said poles, one of said poles being on one side of said probe and the axis of rotation passing through the other of said poles, the probe, when energized creating said magnetic field extending between poles principally in a region adjacent to that one side of the probe and in the region adjacent to one side of said hole, said coil being mounted on said arm on said one side of said probe;

(b) energizing said coil to provide said magnetic field;

(c) rotating said probe by means of a stepping drive arrangement about its axis of rotation in a step-wise fashion; and (d) generating at the end of each step of stepped rotation a first signal representative of the energy of said magnetic field dissipated in said workpiece by detecting the energy supplied to said coil;

(e) generating a second signal representative of the energy dissipated in defect free regions of said workpiece;

(f) comparing said first and second signals and providing a third signal representing any difference between said first and second signals;

(g) digitizing said third signal, (h) storing said third signal in digital form while said probe is rotating; and (i) displaying a graphical plot of the variation of said third signal with the rotational position of said probe.

* * * * *